United States Patent [19]

McGowan et al.

[11] Patent Number: 5,348,470
[45] Date of Patent: Sep. 20, 1994

[54] FIBER-OPTIC ILLUMINATED DENTAL MIRROR

[76] Inventors: Nancy J. McGowan; Robert A. McGowan, both of 204 Sweetbriar St., Pittsburgh, Pa. 15211

[21] Appl. No.: 11,232

[22] Filed: Jan. 29, 1993

[51] Int. Cl.$^5$ .......................... A61C 1/00; A61C 3/00; A61B 1/24
[52] U.S. Cl. ........................ 433/30; 433/29; 433/31
[58] Field of Search ............... 433/29, 30, 31; 128/11, 128/22

[56] References Cited

U.S. PATENT DOCUMENTS

| | | | |
|---|---|---|---|
| 1,533,605 | 4/1925 | Pelton et al. | 433/29 |
| 3,032,879 | 5/1962 | Lafitte | 433/30 |
| 3,614,415 | 10/1971 | Edelman | 433/29 |
| 3,683,503 | 8/1972 | Klein | 433/29 |
| 5,139,420 | 8/1992 | Walker | 433/31 |
| 5,139,421 | 8/1992 | Verderber | 433/30 |

FOREIGN PATENT DOCUMENTS

| | | | |
|---|---|---|---|
| 1932912 | 1/1971 | Fed. Rep. of Germany | 433/30 |
| 2650498 | 2/1991 | France | 433/31 |
| 1280339 | 7/1972 | United Kingdom | 433/29 |

*Primary Examiner*—Gene Mancene
*Assistant Examiner*—Cindy A. Cherichetti
*Attorney, Agent, or Firm*—William J. Ruano

[57] ABSTRACT

A fiber optic cable attached alongside or extending through the handle of a dental mirror to provide a source of illumination to the mirror. An end of the fiber optic cable is projected towards the mirror. Such end is either flat, shaped as a lens or having a lens attached thereto.

2 Claims, 2 Drawing Sheets

FIBER-OPTIC ILLUMINATED DENTAL MIRROR

BACKGROUND OF THE INVENTION

At present, most dental procedures are done large, overhead projection light source which focuses the light beam onto the patient's mouth using concave mirrors. Within the mouth, detailed examination is done using a small, circular dental mirror affixed at the end of a handle, This mirror reflects the overhead light beam to the area of the mouth being studied, and also reflects the illuminated image back to the eye(s) of the dental technician or dentist. In order to concentrate the light further, or to get an enlarged image, one can use a mirror with a concave reflecting surface. Furthermore, an overhead light requires frequent adjustment which increases the danger of contamination.

After use with a patient, the hand-held dental mirror is autoclaved to sterilize it, to prevent infection and contamination of the next patient for which it is used. Although dental personnel now typically wear gloves, masks, and even goggles to avoid infectious diseases, this mainly protects the dental person, and only indirectly protects each patient. If an overhead lamp is used for illumination, the redirection or refocusing of this lamp requires hand contact by the dental person, and this can lead to cross-contamination of patients. In order to minimize this cross-contamination, a variety of handle covers have been devised and commercialized.

SUMMARY OF THE INVENTION

The present invention relates to an apparatus to overcome the above-mentioned disadvantages and to provide concentrated light inside the patient's mouth during dentistry procedures. This has many advantages with respect to present art of dental lighting, including no heat or light on the patient's face or in the patient's eyes, and no cross-contamination by the dental personnel from hand contact with an overhead light during the dental procedure.

The present invention consists, basically, of a fiber-optic illuminated dental mirror. The light source can be portable (battery powered) or fixed (AC line powered).

DESCRIPTION OF THE PREFERRED EMBODIMENTS

Figure 1:
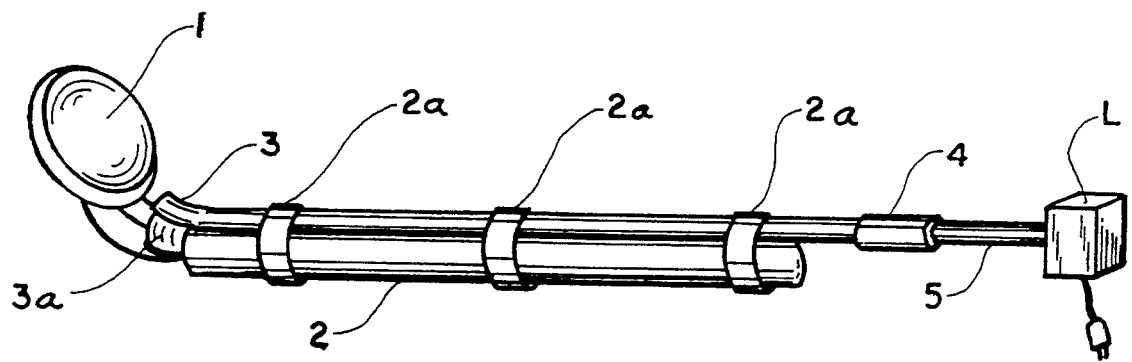
FIG. 1 shows a first embodiment of the invention.

The first embodiment of the present invention is shown in FIG. 1. A commercial dental mirror 1, mounted on a handpiece or handle 2 has affixed by clamps 2a, a metal-sheathed fiber-optic bundle 3. The fiber-optic bundle is connected to a flexible fiber-optic cable via a metal, plastic or elastomeric coupling 4. The fiber-optic cable 5 is illuminated by a light source L. Plastic back-up material 3a may be used for stability.

Figure 2:
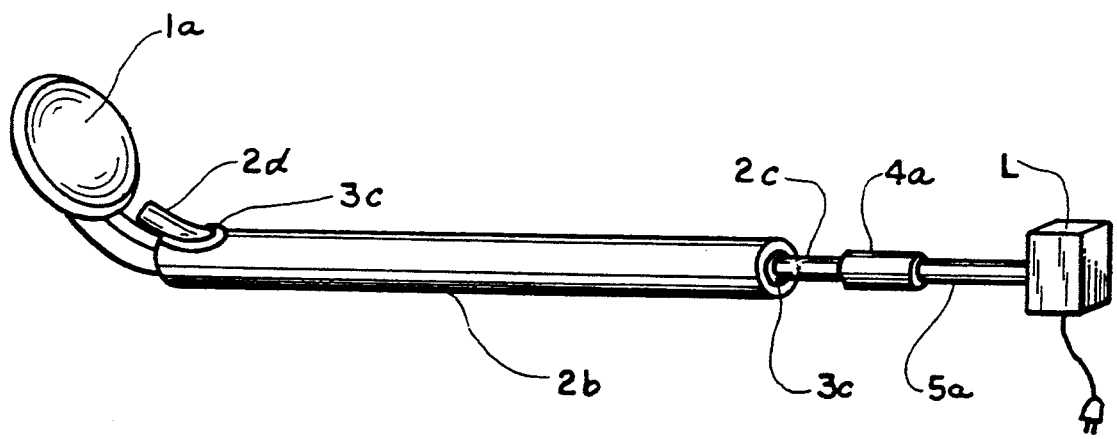
FIGS. 2 & 3 show a second and third embodiment of the invention.

An improved embodiment is shown in FIG. 2, A hollow plastic or stainless steel handpiece 2b with circular or hexagonal crosssection contains, therein a glass fiber-optic bundle 2c. These are seamlessly connected by autoclave-resistant epoxy cement at both ends, 3c 3c. The fiber-optic cable 5a is illuminated by a light source $L^1$.

Figure 3:
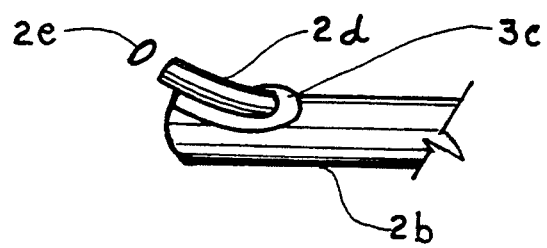

The free end 2d of bundle 2c can be polished flat or into the shape of a lens or a lens 2e may be attached to its end as shown in FIG. 3. The light beam from extension 2d is reflected by mirror 1a, and the assembly is maneuvered in the patient's mouth to reflect light off a typical tooth. The illuminated image of the tooth then reflects back via mirror 1a to the eye of the dental worker. Since many dental offices may have light sources already available, an adapter can be provided to couple the internal diameter of the output light port on the light source to the flexible fiber-optic conductor. The curved, mirror end of the handle may be detachably secured to the handle by a screwed or slip fit.

Figure 4:
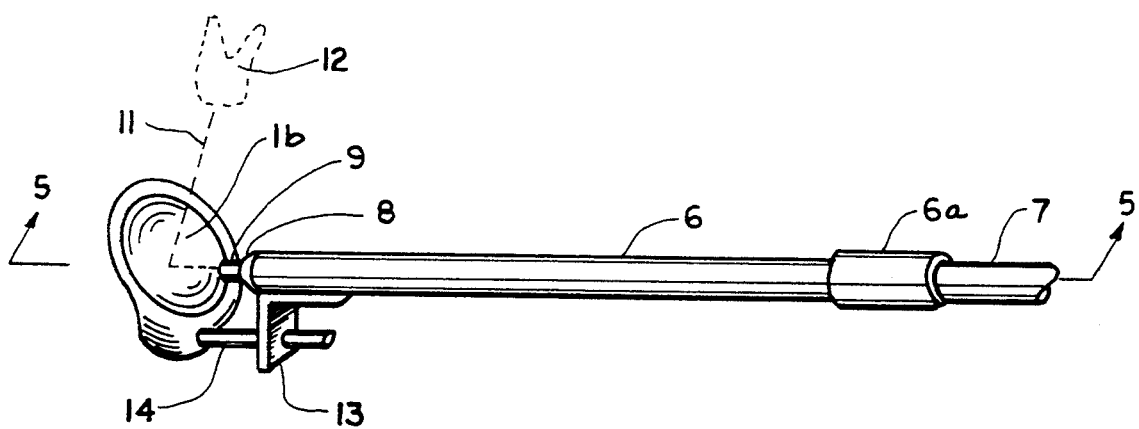
FIGS. 4 and 5 show a fourth embodiment.
Figure 5:
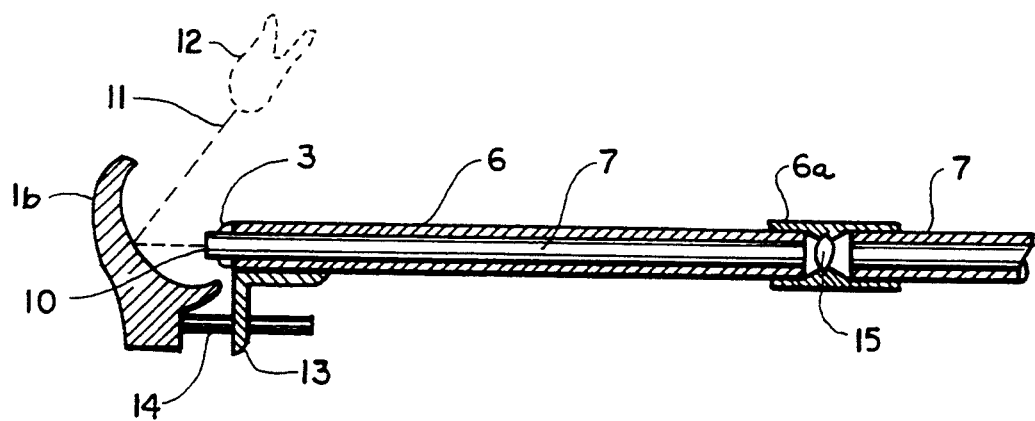

FIGS. 4 and 5 show a fourth embodiment of the invention. A hollow handle or handpiece 6 of circular (or hexagonal) cross-section encloses a glass fiber-optic bundle 7, at least one end of which, such as at 3, may be seamlessly connected by autoclave-resistant epoxy cement.

An angular protrusion 13, by means of rod 14, is firmly fixed to the handpiece 6 by welding, brazing or soldering. This protrusion 13 has a tapped hole through which rod 14 extends, which rod is connected to a dental mirror 1b. The opposite end of the handpiece is connected, by means of an elastomeric coupling 6a, to a flexible fiber-optic cable 6b which is connected to a light source (not shown).

In order to increase the optical energy coupling between the fiber-optic bundle 7 in handpiece 6 and that in the extension 6b thereof, a lens, such as a spherical lens 15, can be inserted in sleeve 6a. The light from its source is coupled to the fiber-optic bundle 7 in sleeve 6. The free end 10 of the bundle 7 can be polished flat or into the shape of a lens. Light from the free end 10 emerges as a beam 11 reflected by mirror 1b and the assembly is maneuvered in the patient's mouth to reflect light off a typical tooth 12. The illuminated image of the tooth 12 then reflects back by mirror 1b to the eye of the dental worker.

While the foregoing are examples of the invention, other modifications can be made within the scope of the claims.

I claim:

1. A fiber optic cable, a dental mirror located at one end of said cable for providing a source of illumination for said dental mirror, together with a handle for supporting said dental mirror at one end of aid handle and for supporting said cable along the length of said handle, said dental mirror being attached to said one end of said handle, together with a lens attached to the other end of said cable, which other end is surrounded by an elastomeric coupling, and a second flexible fiber-optic cable having one end surrounded by said elastomeric coupling and the other end illuminated by said light source.

2. The combination recited in claim 1 wherein said handle surrounds said first mentioned optic cable.

* * * * *